United States Patent
Roth

(10) Patent No.: US 7,692,773 B2
(45) Date of Patent: Apr. 6, 2010

(54) LIGHT EMITTING DIODE BASED MEASUREMENT SYSTEMS

(75) Inventor: Wayne D. Roth, Leander, TX (US)

(73) Assignee: Luminex Corporation, Austin, TX (US)

( * ) Notice: Subject to any disclaimer, the term of this patent is extended or adjusted under 35 U.S.C. 154(b) by 490 days.

(21) Appl. No.: 10/896,181

(22) Filed: Jul. 21, 2004

(65) Prior Publication Data

US 2005/0030519 A1 Feb. 10, 2005

Related U.S. Application Data

(60) Provisional application No. 60/492,686, filed on Aug. 5, 2003.

(51) Int. Cl.
*G01P 3/36* (2006.01)
(52) U.S. Cl. ..................... 356/28.5; 356/28
(58) Field of Classification Search ............... 356/28.5, 356/3.01–3.15, 4.01–4.1, 5.01–5.15, 6–22, 356/28, 28.5, 128, 128.5
See application file for complete search history.

(56) References Cited

U.S. PATENT DOCUMENTS

| | | | |
|---|---|---|---|
| 4,687,327 A | | 8/1987 | Wheeless |
| 5,701,172 A | * | 12/1997 | Azzazy ................. 356/28 |
| 5,736,330 A | | 4/1998 | Fulton |
| 5,784,154 A | * | 7/1998 | Pawliszyn ............. 356/128 |
| 5,867,257 A | * | 2/1999 | Rice et al. ............. 356/28.5 |
| 5,981,180 A | | 11/1999 | Chandler et al. |
| 6,046,807 A | | 4/2000 | Chandler |
| 6,057,107 A | | 5/2000 | Fulton |

(Continued)

FOREIGN PATENT DOCUMENTS

WO 94/14053 6/1994

(Continued)

OTHER PUBLICATIONS

Adam et al., "Microfluidic integration on detector arrays for absorption and fluorescence micro-spectrometers," Sensors and Actuators A, vol. 104, 2003, pp. 25-31.

(Continued)

*Primary Examiner*—Thomas H Tarcza
*Assistant Examiner*—Luke D Ratcliffe
(74) *Attorney, Agent, or Firm*—Charles D. Huston; Mollie E. Lettang; Daffer McDaniel, LLP

(57) ABSTRACT

Various light emitting diode (LED) based measurement systems and methods are provided. One system includes one or more arrays of LEDs arranged along a flow path of a sample. The array(s) are configured to illuminate the sample as the sample moves along the flow path. The system also includes one or more detectors configured to detect light resulting from illumination of the sample by the array(s). One method includes illuminating a microsphere at different positions along a flow path of the microsphere. The method also includes detecting light resulting from the illumination to produce individual output signals corresponding to the illumination at the different positions. The method further includes combining the individual output signals to produce a single output signal having a signal-to-noise ratio that is greater than a signal-to-noise ratio of the individual output signals.

47 Claims, 5 Drawing Sheets

U.S. PATENT DOCUMENTS

| | | | |
|---|---|---|---|
| 6,139,800 | A | 10/2000 | Chandler |
| 6,249,341 | B1 | 6/2001 | Basiji et al. |
| 6,268,222 | B1 | 7/2001 | Chandler et al. |
| 6,366,354 | B1 | 4/2002 | Chandler |
| 6,411,904 | B1 | 6/2002 | Chandler |
| 6,449,562 | B1 | 9/2002 | Chandler et al. |
| 6,514,295 | B1 | 2/2003 | Chandler et al. |
| 6,524,793 | B1 | 2/2003 | Chandler et al. |
| 6,528,165 | B2 | 3/2003 | Chandler |
| 7,126,695 | B2 * | 10/2006 | Tansey ............ 356/486 |
| 2003/0026468 | A1 | 2/2003 | Chu et al. |
| 2003/0204330 | A1 * | 10/2003 | Allgeyer ............ 702/32 |
| 2004/0075824 | A1 * | 4/2004 | Belenkii et al. ........ 356/28 |
| 2004/0223135 | A1 * | 11/2004 | Ortyn et al. .......... 356/28 |

FOREIGN PATENT DOCUMENTS

| | | |
|---|---|---|
| WO | 99/42809 | 8/1999 |
| WO | 09/046548 | 6/2003 |

OTHER PUBLICATIONS

International Search Report, PCT/US2004/024987, mailed Dec. 22, 2004.

* cited by examiner

LIGHT EMITTING DIODE BASED MEASUREMENT SYSTEMS

PRIORITY CLAIM

This application claims priority to U.S. Provisional Application No. 60/492,686 entitled "Light Emitting Diode Based Measurement System," filed Aug. 5, 2003.

BACKGROUND OF THE INVENTION

1. Field of the Invention

This invention generally relates to light emitting diode based measurement systems. Certain embodiments relate to a measurement system that includes one or more arrays of light emitting diodes arranged along a flow path of microspheres or other fluorescence emitting samples.

2. Description of the Related Art

Generally, flow cytometers provide measurements of fluorescence intensity of laser excited polystyrene beads or cells as they pass linearly through a flow chamber. However, flow cytometers can also be used to provide measurements of one or more properties of other particles. Some systems are configured to perform measurements on the level of light scattered by particles at 90 or 180 degrees to the excitation source, two or more measurements of fluorescence used to determine classification, which is the particle "identity," and additional fluorescence measurements known as "reporters," typically used to quantify chemical reactions of interest. Each of the fluorescent measurements is made at different wavelengths.

One excitation laser commonly used in flow cytometers is a 532 nm solid-state laser. Such a laser tends to have a relatively large beam diameter (e.g., about 0.3 mm). A lens system may be used to reduce the beam diameter of the laser to an elliptical spot having lateral dimensions of about 75 µm by about 25 µm. The elliptical spot lies within an optical sensor's detection window. There are, however, several disadvantages to the 532 nm laser. For example, the 532 nm laser is quite expensive (e.g., about $5,500 each), consumes significant electrical power, and generates a substantial amount of heat.

Another laser that is used in commercially available flow cytometers is an argon ion 488 nm laser. There are, however, also several disadvantages to this laser. For example, it is relatively large (e.g., occupying several cubic feet), requires a massive power supply, and needs constant forced air cooling to maintain stability. There are other smaller and less expensive lasers that are commercially available. However, these lasers are generally unsuitable for flow cytometry. For example, dye lasers may burn out too quickly to be used as suitable light sources in a flow cytometer based measurement system. In addition, He—Cd lasers may be too noisy for flow cytometer measurements.

Furthermore, the beam profile of a laser diode may be relatively uneven compared to that of a standard argon ion laser. The unevenness presents a significant obstacle for flow analyzers because fluorescence measurements depend upon substantially uniform excitation among particles and cells. Some efforts have been made to optically correct the beam by steering outside peaks in the beam profile toward the center using beam shaping optics such as prismatic expanders, beam shaping expanders, and micro lens arrays. However, such optics are relatively expensive and add to the manufacturing complexity of the flow cytometers. In addition, even when expensive and complex beam shaping optics are used, the resulting beam profile may still be unsatisfactory (e.g., a 10% to 15% variation in energy intensity across the flow path).

Accordingly, it may be advantageous to provide an excitation source for a flow cytometry based measurement system that is less expensive, consumes less power, generates less heat, is smaller in size, has a longer lifetime, is less noisy, and/or is less weak than the lasers mentioned above. The excitation source also preferably has a wavelength that is suitable for flow cytometer type measurements.

SUMMARY OF THE INVENTION

The present invention relates to a measurement system that incorporates several inexpensive light emitting diodes (LEDs) as an effective excitation source. By arranging multiple LED dies in an array and integrating along the length of the resultant electrical pulse, the signal-to-noise (S/N) ratio may be improved such that fluorescent measurements are possible. For example, when the resultant electrical pulse is lengthened proportional to the number of LED dies, the S/N ratio of the signal integrated by the digital signal processor (DSP) or another processor is increased making the inexpensive LEDs an effective alternative to the more expensive diode lasers currently used in measurement systems. In addition, multiple linear arrays of LEDs can be used to illuminate the length of the cuvette for either more light of the same wavelength (e.g., to provide increased brightness over one array), to simultaneously illuminate a sample with multiple wavelengths, or both. Furthermore, the array of LEDs reduces the complexity, cost, and size of the measurement system.

One particular embodiment relates to a measurement system that includes an array of LEDs arranged along a flow path of a sample. The array is configured to illuminate the sample as the sample moves along the flow path. The measurement system also includes one or more detectors configured to detect light resulting from illumination of the sample by the array. The sample may include microspheres. In addition, the system may be configured as a flow cytometer type measurement system.

Individual LEDs of the array may be configured to illuminate the sample with approximately the same wavelength or wavelengths of light. In addition, individual LEDs of the array are configured to illuminate the sample at different positions along the flow path. Furthermore, individual LEDs of the array may be positioned in a substantially linear arrangement such that the individual LEDs are configured to illuminate the sample at approximately the same angle of illumination. Moreover, individual LEDs of the array may be positioned such that gaps are arranged between active areas of the individual LEDs and such that the array is further configured to illuminate the sample with a series of discrete light pulses as the sample moves along the flow path.

In another embodiment, individual light emitting diodes of the array are positioned in a two-dimensional array such that a first portion of the individual LEDs are configured to illuminate the sample at different positions along the flow path at approximately the same angle of illumination and such that a second portion of the individual LEDs are configured to illuminate the sample at one of the different positions along the flow path at different angles of illumination. In a further embodiment, individual LEDs of the array are configured to illuminate the sample at a single position along the flow path. In one such embodiment, the individual LEDs are further configured to illuminate the sample at the single position with substantially the same wavelength of light. In a different such embodiment, the individual LEDs are further configured to illuminate the sample at the single position with different wavelengths of light.

In some embodiments, the system may also include one or more additional arrays of LEDs. The array and the one or more additional arrays are arranged along different portions of the flow path. In one such embodiment, the one or more additional arrays are configured to illuminate the sample as the sample moves along the flow path with a wavelength of light that is different than a wavelength of light of the array. In another such embodiment, the one or more additional arrays are configured to illuminate the sample as the sample moves along the flow path at an angle of illumination that is different than an angle of illumination of the array.

In a different embodiment, the array and the one or more additional arrays may be arranged along the same portion of the flow path. In such an embodiment, the one or more additional arrays are configured to illuminate the sample as the sample moves along the flow path with a wavelength of light that is different than a wavelength of light of the array. In another such embodiment, the one or more additional arrays are configured to illuminate the sample as the sample moves along the flow path at an angle of illumination that is different than an angle of illumination of the array.

The one or more detectors are configured to generate output signals that are representative of the light resulting from the illumination of the sample. In such an embodiment, the system may also include a processor. The processor may be configured to combine the output signals corresponding to a single microsphere of the sample into a single output signal having a S/N ratio that is greater than a S/N ratio of each of the output signals. In another such embodiment, the processor may be configured to combine the output signals corresponding to a single microsphere of the sample into a single output signal having a pulse length that is greater than a pulse length of each of the output signals. In this embodiment, the pulse length of the single output signal is approximately proportional to the number of light emitting diodes in the array that produced said each of the output signals.

In one embodiment, the system may include one or more lenses configured to direct light from the LEDs onto the flow path. In another embodiment, the system may include one or more lenses configured to collect the light resulting from the illumination and to direct the collected light onto substantially an entire area of a photosensitive surface of the one or more detectors. In some embodiments, the system may include one or more lenses configured to collect the light resulting from the illumination and to direct the collected light onto a photosensitive surface of the one or more detectors directly. In other embodiments, the system may include one or more lenses configured to collect the light resulting from the illumination and to direct the collected light onto a photosensitive surface of the one or more detectors indirectly using one or more fiber optic cables.

In an embodiment, the light resulting from the illumination includes fluorescence emitted by the sample. In a different embodiment, the light resulting from the illumination includes light scattered by the sample. In yet another embodiment, the light resulting from the illumination may include fluorescence emitted by the sample and light scattered by the sample. In some embodiments, the system may include an additional light source that is configured to illuminate the sample as the sample moves along the flow path. In such embodiments, the light resulting from the illumination of the sample by the array may include fluorescence emitted by the sample, and light resulting from illumination of the sample by the additional light source may include light scattered by the sample. Each of the embodiments of the system described above may be further configured as described herein.

Another embodiment relates to a measurement method that includes illuminating a microsphere at different positions along a flow path of the microsphere. The method also includes detecting light resulting from illuminating the microsphere to produce individual output signals corresponding to the illumination of the microsphere at the different positions. In addition, the method includes combining the individual output signals to produce a single output signal having a S/N ratio that is greater than a S/N ratio of the individual output signals. The single output signal also has a pulse length that is greater than a pulse length of each of the individual output signals.

In one embodiment, illuminating the microsphere includes illuminating the microsphere with one or more arrays of LEDs arranged along the flow path of the microsphere. The one or more arrays are configured to illuminate the microsphere as the microsphere moves along the flow path. In some embodiments, illuminating the microsphere includes illuminating the microsphere at the different positions with approximately the same wavelength or wavelengths of light. In another embodiment, illuminating the microsphere includes illuminating the microsphere at the different positions at approximately the same angle of illumination. In an additional embodiment, illuminating the microsphere includes illuminating the microsphere at the different positions with a series of discrete light pulses.

In another embodiment, illuminating the microsphere includes illuminating the microsphere at one of the different positions at multiple angles of illumination with multiple individual LEDs. In one such embodiment, the multiple individual LEDs generate light of substantially the same wavelength. In a different such embodiment, the multiple individual LEDs generate light of different wavelengths.

In an embodiment, the different positions may be arranged along a first portion of the flow path. In such an embodiment, illuminating the microsphere may include illuminating the microsphere at the different positions with a first wavelength of light. The method may further include illuminating the microsphere at additional positions along a second portion of the flow path of the microsphere with a second wavelength of light that is different than the first wavelength of light. In a different such embodiment, illuminating the microsphere may include illuminating the microsphere at the different positions at a first angle of illumination, and the method may include illuminating the microsphere at additional positions along a second portion of the flow path of the microsphere with a second angle of illumination that is different than the first angle of illumination.

In some embodiments, illuminating the microsphere may include illuminating the microsphere at the different positions with two or more arrays of LEDs configured to produce light having different wavelengths. In another embodiment, illuminating the microsphere may include illuminating the microsphere at the different positions with two or more arrays of LEDs arranged at different angles of illumination. In one such embodiment, the two or more arrays are configured to illuminate the microsphere with a different wavelength of light at each of the different angles of illumination.

In a further embodiment, detecting the light may include detecting the light resulting from illumination of the microsphere with one or more detectors. In additional embodiments, the method may include collecting the light resulting from illuminating the microsphere and directing the collected light directly onto a photosensitive surface of one or more detectors. The one or more detectors perform detecting the light as described above. In another embodiment, the method may include collecting the light resulting from illumination of the microsphere and directing the collected light indirectly onto a photosensitive surface of one or more detectors using one or more fiber optic cables. In this embodiment, the one or more detectors also perform detecting the light as described above.

In one embodiment, the light resulting from illumination of the microsphere may include fluorescence emitted by the microsphere. In a different embodiment, the light resulting from illumination of the microsphere may include light scattered by the microsphere. In yet another embodiment, the light resulting from illumination of the microsphere may include fluorescence emitted by the microsphere and light scattered by the microsphere. Each of the embodiments of the method described above may include any other steps described herein.

An additional embodiment relates to a computer-implemented method. This method includes combining individual output signals to produce a single output signal having a S/N ratio that is greater than a S/N ratio of the individual output signals. The single output signal also has a pulse length that is greater than a pulse length of each of the individual output signals. The individual output signals correspond to light resulting from illumination of a microsphere at different positions along a flow path of the microsphere.

In one embodiment, the illumination may include illumination by an array of LEDs arranged along the flow path of the microsphere. The array is configured to illuminate the microsphere as the microsphere moves along the flow path. In another embodiment, the individual output signals are produced by one or more detectors.

In an additional embodiment, the illumination includes illumination at the different positions with approximately the same wavelength or wavelengths of light. In another embodiment, the illumination may include illumination at the different positions at approximately the same angle of illumination. In some embodiments, the illumination includes illumination at the different positions at different angles of illumination using approximately the same wavelength of light. In other embodiments, the illumination includes illumination at the different positions at different angles of illumination using different wavelengths of light. In yet another embodiment, the illumination includes a series of discrete light pulses.

In one embodiment, the light resulting from the illumination includes fluorescence emitted by the microsphere. In another embodiment, the light resulting from the illumination includes light scattered by the microsphere. In a different embodiment, the light resulting from the illumination includes fluorescence emitted by the microsphere and light scattered by the microsphere. Each of the embodiments of the method described above may include any other steps described herein.

BRIEF DESCRIPTION OF THE DRAWINGS

Other objects and advantages of the invention will become apparent upon reading the following detailed description and upon reference to the accompanying drawings in which.

Figure 1:
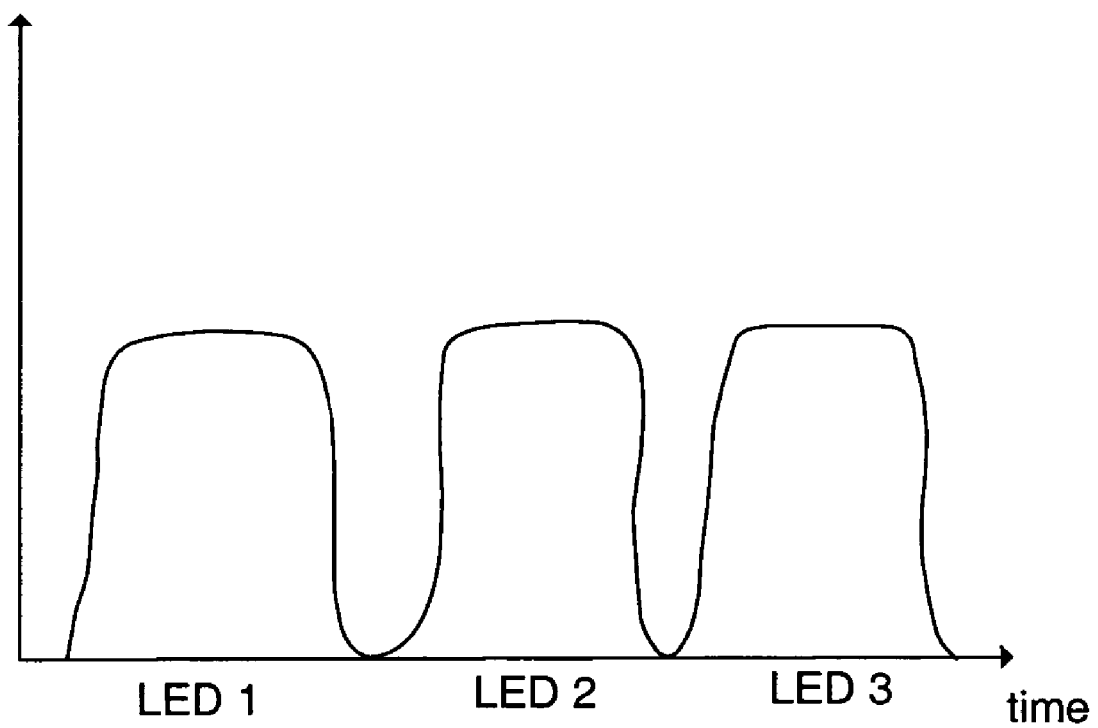
FIG. 1 is a graph illustrating one example of a series of pulses that may be generated by a detector configured to detect fluorescent emissions from microspheres that are excited with illumination from 3 LED dies.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Although the embodiments are described herein with respect to microspheres or polystyrene beads, it is to be understood that the measurement systems and methods may also be used with microparticles, beads, microbeads, latex particles, latex beads, fluorescent beads, fluorescent particles, colored particles, colored beads, and cells. The microspheres may serve as vehicles for molecular reactions. Examples of appropriate microspheres, beads, and particles are illustrated in U.S. Pat. Nos. 5,736,330 to Fulton, 5,981,180 to Chandler et al., 6,057,107 to Fulton, 6,268,222 to Chandler et al., 6,449,562 to Chandler et al., 6,514,295 to Chandler et al., 6,524,793 to Chandler et al., and 6,528,165 to Chandler, which are incorporated by reference as if fully set forth herein. The measurement systems and methods described herein may be used with any of the microspheres, beads, and particles described in these patents. In addition, microspheres for use in flow cytometry may be obtained from manufacturers such as Luminex Corp., Austin, Tex. The terms "sample" and "microspheres" are used interchangeably herein.

In addition, although embodiments are described herein with respect to light emitting diodes (LEDs), it is to be understood that the methods and systems described herein may also be used with any other light sources, and particularly with inexpensive, compact light sources having relatively low energy density and low power consumption.

Recent developments in LED technology have yielded inexpensive devices with significantly increased light intensity over previously available units. Still, the energy density is decades below that of a diode laser. If a single LED is used as the excitation source in a flow cytometer, the resultant fluorescent signal-to-noise ratio (S/N) from the beads may not exceed the detection limit of the photodetectors in the system. Therefore, flow cytometer type measurements may not be possible with a single LED used as the excitation source.

One might think that it would be possible to overcome the lower energy density by combining a 2-dimensional matrix of LED devices and image them to a single 75 µm by 25 µm spot, which is the spot size that is currently used in flow cytometer systems. However, due to a well known optical property for a single lens system, the energy density at the image plane cannot exceed that of the source's energy density. Thus, using a conventional single lens system, it is not possible to combine the output power of multiple LEDs to increase the energy density at the image plane (over that of a single LED).

While it is not possible to achieve a laser's energy density using a simple lens design with a 2-dimensional matrix of LEDs, the geometry of flow cytometers lends itself to another configuration for achieving higher S/N ratios than that which would result by using a single LED die as the illumination source.

In a flow cytometer, the fluorescently tagged polystyrene beads flow through the flow chamber (e.g., in a vertical direction) and pass through the detection window. A light source illuminates the polystyrene beads while they are passing through the detection window. The illumination may cause the polystyrene beads to emit fluorescent light having one or more wavelengths or wavelength bands. Fluorescence emitted by the polystyrene beads is focused on a photodetector using one or more lenses. The photodetector's output current is proportional to the fluorescent light impinging on it and results in a current pulse. The current pulse may be converted to a voltage pulse, low pass filtered, and then digitized by an A/D converter. A processor such as a digital signal processor (DSP) integrates the area under the pulse to provide a number which represents the magnitude of the fluorescence.

Since noise is a random function, through integration, its effects are attenuated as the pulse length is extended. Thus, if the pulse can be stretched, while maintaining the same amplitude and overall system gain, the S/N ratio of the photodetector output will increase. As the S/N ratio increases through this mechanism, the system will require less and less energy density from the excitation source to produce measurable fluorescence readings.

As stated earlier, polystyrene beads flow through a flow cytometer in a generally linear direction (e.g., vertically) along a flow path. Thus, multiple LED dies can be arranged along the flow path of the sample to illuminate the sample as it moves along the flow path. In some embodiments, the array of LEDs may be positioned in an approximately linear arrangement such that the individual LEDs illuminate the sample at substantially the same angle of illumination. The individual LEDs of the array may provide illumination for one measurement (e.g., one fluorescence measurement). In this manner, the time of bead illumination for a single measurement is extended proportionally to the number of LED dies in the array. If a lens system, which may include one or more lenses, focuses substantially the entire length of the detection window on the photosensitive surface of the optical detector or detectors, then the pulse detected by the detector (s) will be advantageously extended approximately proportionally to the number of individual LEDs in the array that produced said each of the output signals that are combined into a single output signal for a microsphere.

The LED dies will likely have relatively small gaps between their active areas and may result in a series of light pulses across the length of the array. Therefore, as shown in FIG. 1 in which the active areas of three LED dies are shown for illustration purposes only, over a period of time a sample will experience a series of discrete light pulses, each produced by a different individual LED of the array. It is to be understood that the number of LED dies in an array may vary greatly, for example, from two LED dies to four or more LED dies. An analog low pass filter downstream of the optics in the processing electronics will tend to smooth out the valleys between the pulses, but the final shape of the composite pulse is immaterial as long as it is substantially time invariant. Integration of the signal performed during an instrument calibration process can be used to normalize the pulse shape. Furthermore, it is important to note that since the gaps between the illuminated areas of the flow path are relatively small, there is little chance that microspheres of the sample will get switched or mixed up from one illuminated area to the next. As such, one can be relatively certain that individual pulses that are combined to produce the high S/N ratio pulse correspond to a single microsphere.

There are several aspects to consider when choosing the number of LEDs in an array. For instance, the magnification of the illuminated area of the flow path will preferably produce an image that fits within the photodetector's active area. In addition, the magnification of the illuminated area of the flow path may approximately match the area of the photosensitive area of the detector(s) such that the length of the pulse is extended to its maximum without loss of signal. For example, as opposed to a single spherical lens, a set of cylindrical lenses may be employed to widen the image strip such that it fills substantially the entire photosensitive area of the detector(s).

Another factor to be taken into consideration is the capability of the digitizer. Most importantly, the processing power and memory capacity of the processor or DSP of the measurement system, which integrates the digitized pulse, may be considered when selecting the number of LEDs in an array. Preferably, the pulse that is produced by illuminating a sample with the array of LEDs is small enough such that it can be appropriately manipulated by the processor. Furthermore, the statistical spacing between the microspheres may also be considered. However, with the typical bead densities used in a flow cytometer type measurement system, the statistical spacing may not be a factor. Lastly, the stray light accumulated by the detector (background) will increase as the photosensitive area of the detector increases.

FIGS. 2-8 are partial cross-sectional side views illustrating various embodiments of an LED based measurement system. It is noted that FIGS. 2-8 are not drawn to scale. In particular, the scale of some of the elements of the figures are greatly exaggerated to emphasize characteristics of the elements. It is also noted that FIGS. 2-8 are not drawn to the same scale. Elements shown in more than one figure that may be similarly configured have been indicated using the same reference numerals. Some elements of the measurement systems such as a fluid pump have not been included in the figures for the sake of clarity.

Figure 2:
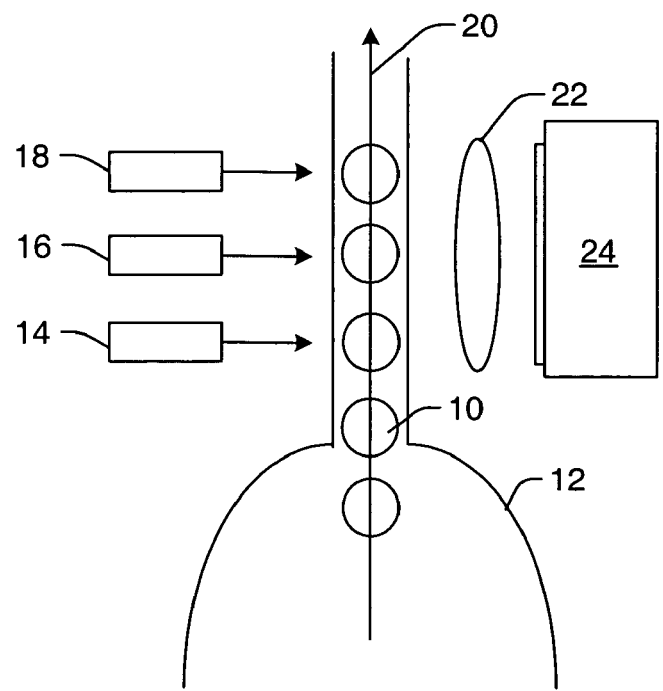
FIGS. 2-8 are schematic diagrams illustrating various embodiments of a light emitting diode based measurement system.

FIG. 2 illustrates one embodiment of an LED based measurement system. As shown in FIG. 2, microspheres 10 may be delivered into cuvette 12 by a fluid pump (not shown). The cuvette provides a detection window through which measurement of the microspheres may be performed. In one example, the cuvette may be a standard quartz cuvette such as that used in standard flow cytometers. Any other suitable type of viewing or delivery chamber, however, may also be used to deliver the sample for analysis. The fluid pump may be, for example, a syringe pump. The fluid pump may draw sample fluid containing the microspheres out of a sample fluid container (not shown) and deliver a drop of the sample fluid into the flow of a sheath fluid (not shown) at approximately the neck down region of the cuvette. The neck down region of the cuvette is the portion of the cuvette that resembles the bottom half of an hour glass.

The microspheres in the sample fluid pass out of the end of the fluid pump and become ensheathed in the sheath fluid. The reduced cross-section of the neckdown region relative to larger portions of the cuvette causes the sheath fluid to accelerate. As a result, the confluence of the sample fluid and the sheath fluid form a coaxial, bi-component stream with the sample fluid forming the inner component of the stream. The sheath fluid elongates the sample fluid thereby causing the microspheres contained therein to flow in substantially single file by the time they reach the focal region of LEDs 14, 16, and 18. Again, although the system is shown in FIG. 2 to include 3 LEDs, it is to be understood that the system may include any other suitable number of LEDs.

LEDs 14, 16, and 18 are arranged in an array along flow path 20 of the sample. The array of LEDs is configured to illuminate the sample as the sample moves along the flow path. As shown in FIG. 2, the LEDs may be positioned in a substantially linear arrangement such that the individual LEDs each illuminate the sample at approximately the same angle of illumination. As further shown in FIG. 2, the LEDs may be arranged such that a microsphere is illuminated by each LED at a different time. Each of the LEDs may illuminate the microspheres with light having approximately the same wavelength or the same range of wavelengths. For example, each of the LEDs may be configured to illuminate the microspheres with blue light. The wavelength or range of wavelengths of light emitted by the LEDs may vary depending upon, for example, the type of sample that is being measured and/or a material associated with the sample (e.g., a material bound to the surface of the sample microspheres). For example, in a different embodiment, LEDs 14, 16, and 18 may be configured to emit green light.

Figure 3:
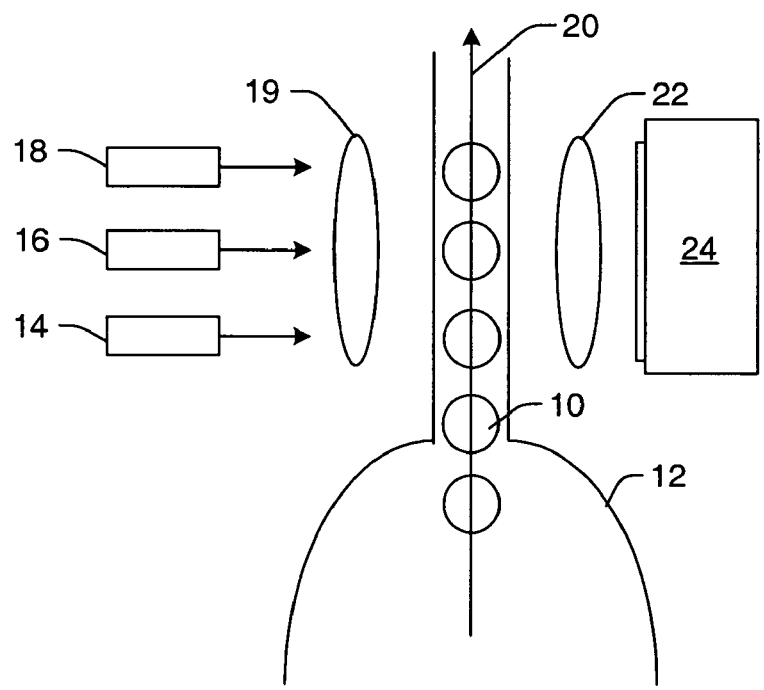
Figure 4:
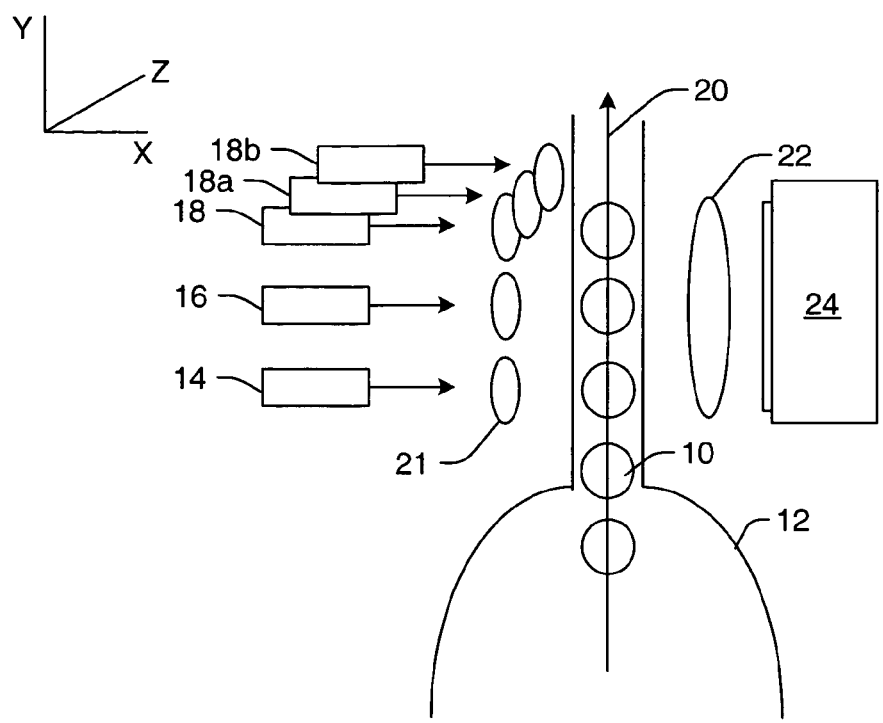

In some embodiments, the system may include one or more lenses configured to direct (e.g., focus) light from the LEDs onto the microspheres or the flowpath. For example, as shown in FIG. 3, the one or more lenses may include single spherical lens 19 configured to direct light from multiple LEDs onto the microspheres or the flowpath. In another example, two or more lenses arranged in a single compound lens may be used to direct light from multiple LEDs onto the microspheres or flowpath. In a further example, as shown in FIG. 4 set of cylindrical lenses 21 may be configured to direct light from multiple LEDs onto the microspheres or the flowpath. Each cylindrical lens of the set may be coupled to one of the LEDs. The one or more lenses may also include any other suitable lens(es) known in the art.

Light scattered by the microspheres or fluorescence emitted by the microspheres due to excitation by the illumination may be collected by lens 22, as shown in FIGS. 2-4. In the embodiment shown in FIGS. 2-4, light scattered or emitted by the microspheres due to illumination by each of the LEDs 14, 16, and 18 is collected by a single lens. In one embodiment, the single lens is a spherical lens. In some embodiments, the lens may include only one lens. Alternatively, the lens may be a compound lens. Although lens 22 is shown in FIGS. 2-4 to be a refractive optical component, it is to be understood that the lens may be replaced with a different type of light directing component (e.g., reflective, catadioptric, etc.). All other lenses described herein may be similarly replaced with other light directing components.

As described above, the LED illumination may be used for measurements of both fluorescence emitted by the microspheres and light scattered by the microspheres. In one such embodiment, the measurements may be made simultaneously with different detectors (such as those shown in FIG. 6 and described further below) arranged at suitable positions with respect to the LEDs. In another embodiment, multiple arrays of LEDs may be used to make different measurements. One such embodiment of multiple arrays of LEDs is described further herein. In a different embodiment, a different (e.g., non-LED) light source (not shown) may be used to provide illumination for light scattering measurements of the sample. The light source used for scattering measurements may include any suitable light source known in the art. In addition, depending on the scattering properties of the sample (e.g., the refractive index of the microspheres), it may be advantageous to use a single light source having a higher energy density than that of an LED such that the scattered light has sufficient intensity to produce adequate output signals.

Lens 22 is configured to direct the collected light onto a photosensitive surface of detector 24. The lens may, in some embodiments, be configured to focus the light onto the photosensitive surface of the detector (e.g., as in an objective lens). In other embodiments, the lens may be configured to image the light onto the photosensitive surface of the detector (e.g., as in an imaging lens). In one embodiment, the detector may be a photo-multiplier tube, a photodiode, a linear array of photosensitive elements, a two-dimensional array of photosensitive elements such as a charge-coupled device (CCD) camera or a time delay integration (TDI) camera, or any other suitable detector known in the art. Another method would be to couple the light from the cuvette, or from lens 22, indirectly to remotely located optical detector(s) via one or more fiber optic cables (not shown).

Output signals of the detector may be processed as described herein. For example, the system may include a processor (not shown in FIG. 2) that may be configured as described herein. In some embodiments, the output signals may be processed to determine an identity of the microspheres. Alternatively, the output signals may be processed to determine information about a reaction taking place on the surface of the microspheres or information about one or more materials associated with the microspheres. The system shown in FIGS. 2-4 may be further configured as described herein.

In some embodiments, the system may include an LED array that includes individual LEDs positioned in a two-dimensional array. In such an array, a first portion of the individual light emitting diodes may be configured to illuminate the sample at different positions along the flow path at approximately the same angle of illumination. A second portion of the individual light emitting diodes may be configured to illuminate the sample at one of the different positions along the flow path at different angles of illumination.

For example, as shown in FIG. 4, the two-dimensional array includes LEDs 14, 16, and 18 that are configured to illuminate the sample at different positions along the flow path at approximately the same angle of illumination. In addition, the array includes LEDs 18, 18*a*, and 18*b* that are configured to illuminate the sample at one of the different positions (or a single position) along the flow path at different angles of illumination. In other words, LEDs 18, 18*a*, and 18*b* are arranged at different positions along the z-axis of the system. The system may also include other LEDs (not shown) that are configured to illuminate the sample at other of the different positions along the flow path at different angles of illumination. Although the z-axis is shown in FIG. 4 to be generally linear, the location of the LEDs in any x-plane may vary depending on, for example, the outer dimensions and/or the shape of the cuvette (e.g., square, rectangular, circular, etc.).

As shown in FIG. 4, individual LEDs of the two-dimensional array arranged along the y-axis are each coupled to one of individual lenses 21 (or one of a micro-array of lenses) that are configured to focus light to different positions along the y-axis. In addition, all three light sources arranged along the z-axis are each coupled to one or more individual lenses such that the light from the light sources is directed to a combined single position along the flow path. The wavelength of each LED along the z-axis may be the same to provide increased power, or different for simultaneous illumination by more than one wavelength. It is noted that although the system shown in FIG. 4 includes LEDs arranged along the y-axis as well as the z-axis in a two-dimensional array, the system may alternatively include LEDs arranged along only the y-axis as shown in FIGS. 2 and 3 or LEDs arranged along only the z-axis.

Figure 5:
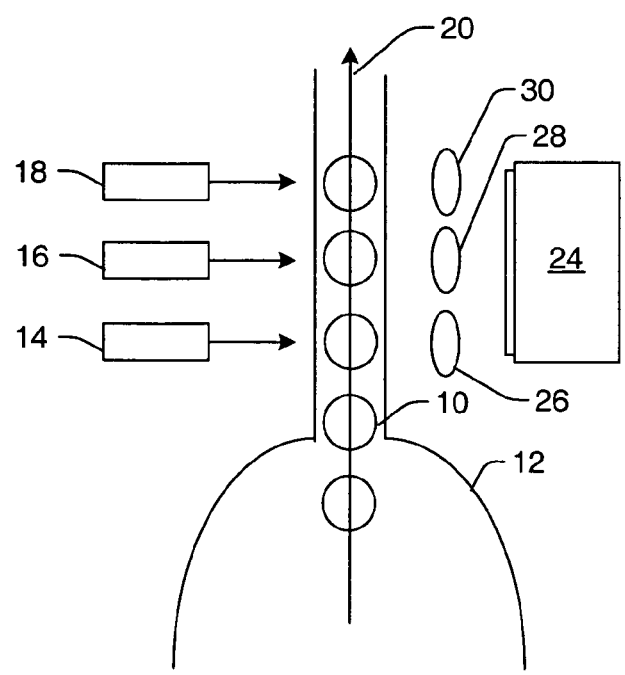

In a different embodiment shown in FIG. 5, light scattered or emitted by the microspheres due to illumination by individual LEDs 14, 16, and 18 may be separately collected by lenses 26, 28, and 30. In other words, each of the lenses collects preferably light resulting from illumination of the sample by only one LED of the array. In one embodiment, lenses 26, 28, and 30 may be cylindrical lenses. However, lenses 26, 28, and 30 may also include any other suitable lenses known in the art. In some embodiments, lenses 26, 28, and 30 may have substantially the same characteristics. Alternatively, lenses 26, 28, and 30 may have different characteristics, which may vary depending upon, for example, characteristics of detector 24. Lenses 26, 28, and 30 may direct (e.g., focus, image, etc.) the collected light onto a photosensitive surface of detector 24 directly, or indirectly (e.g., via a fiber optic cable). Therefore, the system may include more than one collecting lens optically coupled to one detector.

In addition, lenses 26, 28, and 30 may direct the collected light onto different areas of the photosensitive surface of detector 24. Furthermore, lenses 26, 28, and 30 may direct the collected light onto an area that is less than the entire area of the photosensitive surface of the detector. However, the lenses preferably focus the collected light onto an area that is approximately equal to the entire area of the photosensitive surface of the detector. In this manner, the pulse length may be extended to approximately its maximum for a given detector thereby increasing the S/N ratio as much as possible. The system shown in FIG. 5 may be further configured as described herein.

Figure 6:
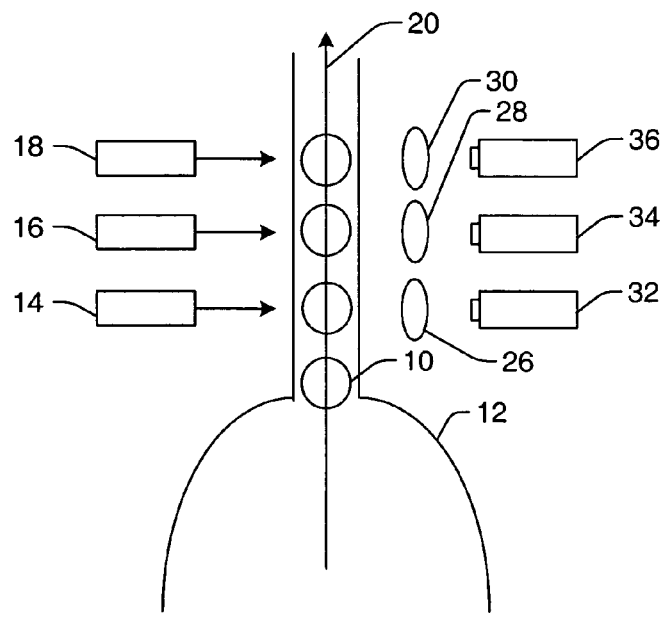

In another embodiment shown in FIG. 6, light scattered or emitted by the microspheres due to illumination by each of LEDs 14, 16, and 18 may be separately collected by lenses 26, 28, and 30. Lenses 26, 28, and 30 may be configured as described above. Light collected by each of the lenses may be directed (e.g., focused, imaged, etc.) onto the photosensitive surface of different detectors. For example, light collected by lens 26 may be directed onto a photosensitive surface of detector 32 directly or indirectly (e.g., via a fiber optic cable). Light collected by lens 28 may be directed onto a photosensitive surface of detector 34 directly or indirectly (e.g., via a different fiber optic cable), and light collected by lens 30 may be directed onto a photosensitive surface of detector 36 directly or indirectly (e.g., via yet another fiber optic cable). The overall photosensitive area of detectors 32, 34, and 36 may be less than the photosensitive area of detector 24 shown in FIGS. 2-5. As such, the signals generated by detectors 32, 34, and 36 may include less stray light or background noise. In this manner, the overall S/N ratio may be increased by using more than one detector. In addition, the lenses may direct the collected light onto an area that is approximately equal to the entire area of the photosensitive surface of the detectors. In this manner, the pulse length may be extended to approximately its maximum for a given system configuration thereby increasing the S/N ratio as much as possible. The system shown in FIG. 6 may be further configured as described herein.

Figure 7:
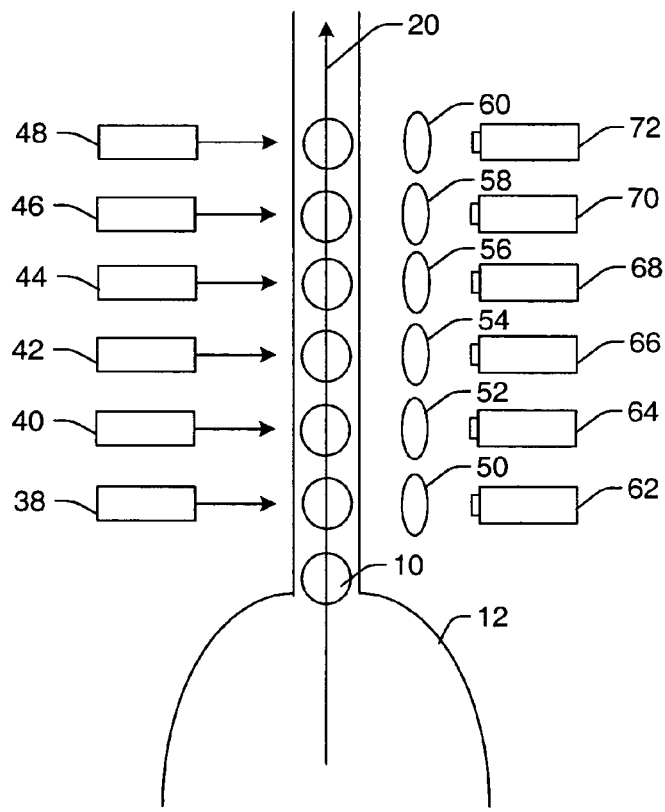

FIG. 7 illustrates yet another embodiment of an LED based measurement system. In this embodiment, the system may be configured to illuminate the microspheres with different wavelengths of light. For example, the system may include more than one array of LEDs. In one embodiment, the system may include a first array of LEDs, which includes LEDs 38, 40, and 42. In addition, the system may include a second array of LEDs, which includes LEDs 44, 46, and 48. Although each array is shown to include three LEDs by way of example, it is to be understood that the number of LEDs in each array may vary depending on, for example, the intensity of the LEDs or the characteristics of the sample. In addition, although the system is shown to include two arrays of LEDs, it is to be understood that the system may include more than two arrays of LEDs.

The first array of LEDs is configured to illuminate the microspheres with a first wavelength or a first plurality of wavelengths of light. The second array of LEDs is configured to illuminate the microspheres with a second wavelength or a second plurality of wavelengths of light. The second wavelength(s) are different than the first wavelength(s). For example, the second wavelength(s) may include blue light, and the first wavelength(s) may include green light. In this manner, the microspheres may be illuminated with different wavelengths of light in one measurement process. The microspheres may emit different types of fluorescence depending on the wavelength of light that is used to excite the microspheres. Therefore, the measurement system may be capable of making multiple measurements in a single measurement process. As such, the measurement capability and sensitivity of the system may be increased as the number of arrays of LEDs are increased.

The system shown in FIG. 7 may also be configured such that light scattered or emitted by the microspheres due to illumination by each of LEDs 38, 40, 42, 44, 46, and 48 may be separately collected by lenses 50, 52, 54, 56, 58, and 60. In one embodiment, lenses 50, 52, 54, 56, 58, and 60 may be cylindrical lenses. However, these lenses may also include any other suitable lenses known in the art. Lenses 50, 52, 54, 56, 58, and 60 may direct (e.g., focus, image, etc.) the collected light onto the photosensitive surfaces of detectors 62, 64, 66, 68, 70, and 72 directly or indirectly (e.g., via a fiber optic cable). In this manner, each lens may be optically coupled to a different detector. In an alternative embodiment, each lens may focus the collected light onto a photosensitive surface of one detector (not shown). The different detectors or the single detector may be configured as described above. In another embodiment, lenses 50, 52, 54, 56, 58, and 60 may be replaced by a single lens, which may be configured as described above. The single lens may be configured to focus the collected light onto a single detector or a plurality of detectors directly or indirectly (e.g., via a fiber optic cable). In a different embodiment, lenses 50, 52, and 54 may be replaced with one lens, and lenses 56, 58, and 60 may be replaced with another lens. In this manner, each array of LEDs may include its own collector lens.

Although the arrays of LEDs shown in FIG. 7 are arranged relatively close together to create an approximately continuous illumination or detection window, it is to be understood that the arrays of the LEDs may be spaced apart along the flow path. In addition, the two arrays of LEDs may be configured to illuminate the microspheres at approximately the same direction (e.g., approximately the same angle of illumination) as shown in FIG. 7. Alternatively, the two arrays of LEDs may be configured to illuminate the microspheres at different directions (e.g., different angles of illumination). In this manner, the arrays of the LEDs may be spaced from each other around a perimeter of the cuvette. In this example, the arrays of the LEDs also may or may not be spaced from each other along the flow path. For example, the arrays of the LEDs may be configured to illuminate the microspheres from different directions at the same time during flow. Alternatively, the subsets of the LEDs may illuminate the microspheres from different directions at different times during flow. The system shown in FIG. 7 may be further configured as described herein.

Figure 8:
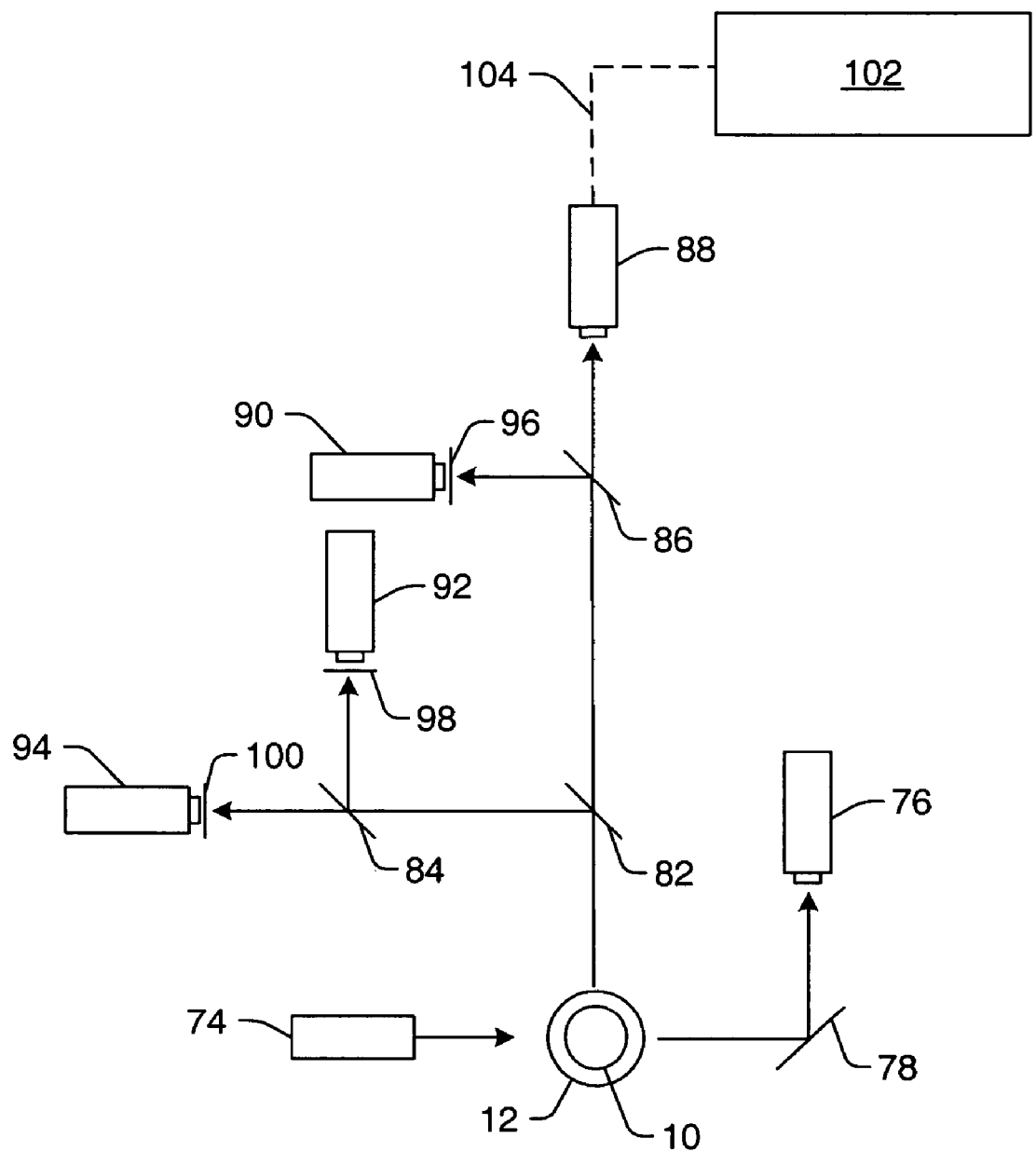

FIG. 8 illustrates an embodiment of an LED based measurement system along a plane through the cross-section of cuvette 12 through which microspheres 10 flow. Therefore, only one LED 74 of an array of LEDs is shown in FIG. 8. In addition, it is to be understood that the detection systems illustrated in FIG. 8 may include one or more detectors as described above. Furthermore, it is to be understood that one or more lenses (not shown) may be optically coupled to each of the detection systems as described above. In a similar manner, it is to be understood that one or more lenses (not shown) may be optically coupled to each of the LEDs in the array as described above. LED 74 and the array of which it is a part of may also be configured as described above.

Light scattered forwardly from microspheres 10 may be directed to detection system 76 by folding mirror 78 or any other suitable light directing component. Alternatively, detection system 76 may be placed directly in the path of the forwardly scattered light. In this manner, the folding mirror or other light directing components may not be included in the system. In one embodiment, the forwardly scattered light may be light scattered by the microspheres at an angle of about 180 degrees from the direction of illumination by LED 74, as shown in FIG. 8. The angle of the forwardly scattered light may not be exactly 180 degrees from the direction of illumination by the LED such that incident light from the LED may not impinge upon the photosensitive area of the detection system. For example, the forwardly scattered light may be light scattered by the microspheres at angles less than or greater than 180 degrees from the direction of illumination (e.g., light scattered at an angle of about 170 degrees, about 175 degrees, about 185 degrees, or about 190 degrees).

Light scattered by the microspheres at an angle of about 90 degrees from the direction of illumination by the LED may also be collected. In one embodiment, this scattered light may be separated into more than one beam of light by one or more beamsplitters. For example, light scattered at an angle of about 90 degrees to the LED may be separated into two different beams of light by beamsplitter 82. The two different beams of light may be separated again by beamsplitters 84 and 86 to produce four different beams of light. Beamsplitters 82, 84, and 86 may include any appropriate beamsplitters known in the art such as dichroic mirrors.

Each of the beams of light may be directed to a different detection system, which may include one or more detectors. For example, one of the four beams of light may be directed to detection system 88. Detection system 88 may be configured to detect light scattered by the microspheres. The other three beams of light may be directed to detection systems 90, 92, and 94. Detection systems 90, 92, and 94 may be configured to detect fluorescence emitted by the microspheres. Each of the detection systems may be configured to detect fluorescence of a different wavelength or a different range of wavelengths. For example, one of the detection systems may be configured to detect green fluorescence. Another of the detection systems may be configured to detect yellow-orange fluorescence, and the other detection system may be configured to detect red fluorescence.

In some embodiments, spectral filters 96, 98, and 100 may be coupled to each of the detection systems. The spectral filters may be configured to block fluorescence of wavelengths other than that which the detection system is configured to detect. Another embodiment (not shown) would be to use one or more fiber optic cables to direct the emitted fluorescent light to one or more detectors. In the case where multiple wavelength LEDs are used as excitation sources along the flow path of the bead or particle, a single detector or detection system could be used for each corresponding emission wavelength by imaging each separate area with multiple fibers. The measurement system shown in FIG. 8 may be further configured as described herein.

The detector's output currents are proportional to the fluorescent light impinging on them and result in current pulses. The current pulses may be converted to voltage pulses, low pass filtered, and then digitized by an A/D converter. Processor 102 such as a DSP integrates the area under the pulse to provide a number which represents the magnitude of the fluorescence. In addition, the processor may perform additional functions described herein (e.g., combining individual output signals to produce a single output signal having a S/N ratio that is greater than a S/N ratio of the individual output signals). As shown in FIG. 8, processor 102 may be coupled to detector 88 via transmission medium 104. Processor 102 may also be coupled to detector 88 indirectly via transmission medium 104 and one or more other components (not shown) such as the A/D converter. The processor may be coupled to other detectors of the system in a similar manner.

Additional examples of measurement systems in which an array of LEDs can be used to replace the excitation sources or light sources currently used in the systems are illustrated in U.S. Pat. Nos. 5,981,180 to Chandler et al., 6,046,807 to Chandler, 6,139,800 to Chandler, 6,366,354 to Chandler, U.S. Pat. No. 6,411,904 to Chandler, 6,449,562 to Chandler et al., and 6,524,793 to Chandler et al., which are incorporated by reference as if fully set forth herein. The measurement systems described herein may also be further configured as described in these patents.

The various measurement system embodiments described above may be used to perform a variety of measurement methods. In one embodiment, a measurement method includes illuminating a microsphere at different positions along a flow path of the microsphere. The method also includes detecting light resulting from illuminating the microsphere to produce individual output signals corresponding to the illumination of the microsphere at the different positions. In addition, the method includes combining the individual output signals to produce a single output signal having a S/N ratio that is greater than a S/N ratio of the individual output signals. The single output signal also has a pulse length that is greater than a pulse length of each of the individual output signals.

In one embodiment, illuminating the microsphere may include illuminating the microsphere with one or more arrays of LEDs arranged along the flow path of the microsphere. The one or more arrays are configured to illuminate the microsphere as the microsphere moves along the flow path. In some embodiments, illuminating the microsphere includes illuminating the microsphere at the different positions with approximately the same wavelength or wavelengths of light. In another embodiment, illuminating the microsphere includes illuminating the microsphere at the different positions at approximately the same angle of illumination. In an additional embodiment, illuminating the microsphere includes illuminating the microsphere at the different positions with a series of discrete light pulses.

In some embodiments, illuminating the microsphere may include illuminating the microsphere at one of the different positions at multiple angles of illumination with multiple individual LEDs. In one such embodiment, the multiple individual LEDs generate light of substantially the same wavelength. In a different such embodiment, the multiple individual LEDs generate light of different wavelengths. In this manner, a microsphere may be illuminated substantially simultaneously with different wavelengths of light or the same wavelength of light at different angles of illumination.

In an embodiment, the different positions may be arranged along a first portion of the flow path. In such an embodiment, illuminating the microsphere may include illuminating the microsphere at the different positions with a first wavelength of light. The method may further include illuminating the microsphere at additional positions along a second portion of the flow path of the microsphere with a second wavelength of light different than the first wavelength of light. In a different such embodiment, illuminating the microsphere may include illuminating the microsphere at the different positions at a first angle of illumination, and the method may include illuminating the microsphere at additional positions along a second portion of the flow path of the microsphere with a second angle of illumination different than the first angle of illumination.

In some embodiments, illuminating the microsphere may include illuminating the microsphere at the different positions with two or more arrays of LEDs configured to produce light having different wavelengths. In another embodiment, illuminating the microsphere may include illuminating the microsphere at the different positions with two or more arrays of LEDs arranged at different angles of illumination. In such embodiments, the two or more arrays may be configured to illuminate the microsphere with a different wavelength of light at each of the different angles of illumination or substantially the same wavelength of light at each of the different angles of illumination.

In a further embodiment, detecting the light may include detecting the light resulting from illumination of the microsphere with one or more detectors. In additional embodiments, the method may include collecting the light resulting from illuminating the microsphere and directing the collected light directly onto a photosensitive surface of one or more detectors. The one or more detectors perform detecting the light as described above. In another embodiment, the method may include collecting the light resulting from illumination of the microsphere and directing the collected light indirectly onto a photosensitive surface of one or more detectors using one or more fiber optic cables. In this embodiment, the one or more detectors also perform detecting the light as described above.

In one embodiment, the light resulting from illumination of the microsphere may include fluorescence emitted by the microsphere. In a different embodiment, the light resulting from illumination of the microsphere may include light scattered by the microsphere. In yet another embodiment, the light resulting from illumination of the microsphere may include fluorescence emitted by the microsphere and light scattered by the microsphere. Each of the embodiments of the method may include any other steps described herein.

An additional embodiment relates to a computer-implemented method that may be performed by various measurement systems described herein. For example, this method may be performed by processor 102 shown in FIG. 8. This method includes combining individual output signals to produce a single output signal having a S/N ratio that is greater than a S/N ratio of the individual output signals. The single output signal also has a pulse length that is greater than a pulse length of each of the individual output signals. The individual output signals correspond to light resulting from illumination of a microsphere at different positions along a flow path of the microsphere.

In one embodiment, the illumination may include illumination by an array of LEDs arranged along the flow path of the microsphere. The array is configured to illuminate the microsphere as the microsphere moves along the flow path. In another embodiment, the individual output signals are produced by one or more detectors.

In an additional embodiment, the illumination includes illumination at the different positions with approximately the same wavelength or wavelengths of light. In another embodiment, the illumination may include illumination at the different positions at approximately the same angle of illumination. In a further embodiment, the illumination may include illumination at the different positions at different angles of illumination using approximately the same wavelength of light. In a different embodiment, the illumination includes illumination at the different positions at different angles of illumination using different wavelengths of light. In yet another embodiment, the illumination includes a series of discrete light pulses.

In one embodiment, the light resulting from the illumination includes fluorescence emitted by the microsphere. In another embodiment, the light resulting from the illumination includes light scattered by the microsphere. In a different embodiment, the light resulting from the illumination includes fluorescence emitted by the microsphere and light scattered by the microsphere. Each of the embodiments of the computer-implemented signal integration method described above may include any other steps described herein.

Program instructions implementing methods such as those described herein may be transmitted over or stored on the carrier medium. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

In an embodiment, a processor may be configured to execute the program instructions to perform a computer-implemented method according to the above embodiments. The processor may take various forms, including a dedicated processing board employing digital signal processing chips or field programmable gate arrays, a personal computer system, mainframe computer system, workstation, network appliance, Internet appliance, personal digital assistant ("PDA"), television system or other device. In general, the term "computer system" may be broadly defined to encompass any device having one or more digital signal processing elements or other processing elements.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired. In the case of a FPGA implementation, the use of high level languages such as VHDL may be employed to design the signal processing circuit embedded within the device.

It will be appreciated to those skilled in the art having the benefit of this disclosure that this invention is believed to provide light emitting diode based measurement systems. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention.

It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A flow cytometer having a particle flow path, comprising:
   an array of light emitting diodes, comprising two or more light emitting diodes serially arranged along said particle flow path, wherein the array is configured to continuously illuminate a particle for a particle illumination time period as the particle moves along the flow path;
one or more detectors configured to detect light resulting from illumination of the particle by the array, wherein the one or more detectors are further configured to generate a plurality of output signals that are representative of the light resulting from the illumination of the particle; and
a processor configured to combine the plurality of output signals corresponding to the particle into a single output signal having a signal-to-noise ratio that is greater than a signal-to-noise ratio of each of the output signals.

2. The flow cytometer of claim 1, wherein individual light emitting diodes of the array are configured to illuminate the particle with approximately the same wavelength or wavelengths of light.

3. The flow cytometer of claim 1, wherein individual light emitting diodes of the array are positioned in a substantially linear arrangement such that the individual light emitting diodes are configured to illuminate the particle at approximately the same angle of illumination.

4. The flow cytometer of claim 1, wherein individual light emitting diodes of the array are configured to illuminate the particle at multiple positions along the flow path during the particle illumination time period.

5. The flow cytometer of claim 4, wherein the individual light emitting diodes are further configured to illuminate the particle during the particle illumination time period with substantially the same wavelength of light.

6. The flow cytometer of claim 1, wherein individual light emitting diodes of the array are positioned such that gaps are arranged between active areas of the individual light emitting diodes and such that the array is further configured to illuminate the particle with a series of discrete light pulses as the particle moves along the flow path resulting in substantially continuous illumination during said time period.

7. The flow cytometer of claim 1, further comprising one or more additional arrays of light emitting diodes, wherein the array and the one or more additional arrays are arranged along different portions of the flow path.

8. The flow cytometer of claim 1, wherein the processor is configured to combine the plurality of output signals corresponding to the particle into a single output signal having a pulse length that is greater than a pulse length of each of the output signals.

9. The flow cytometer of claim 8, wherein the pulse length of the single output signal is approximately proportional to the number of light emitting diodes in the array that produced said each of the output signals.

10. The flow cytometer of claim 1, further comprising one or more lenses configured to direct light from the light emitting diodes onto the flow path.

11. The flow cytometer of claim 1, further comprising one or more lenses configured to collect the light resulting from the illumination and to direct the collected light onto substantially an entire area of a photosensitive surface of the one or more detectors.

12. The flow cytometer of claim 1, further comprising one or more lenses configured to collect the light resulting from the illumination and to direct the collected light onto a photosensitive surface of the one or more detectors directly.

13. The flow cytometer of claim 1, wherein the light resulting from the illumination comprises fluorescence emitted by the particle.

14. The flow cytometer of claim 1, wherein the light resulting from the illumination comprises light scattered by the particle.

15. The flow cytometer of claim 1, wherein the light resulting from the illumination comprises fluorescence emitted by the particle and light scattered by the particle.

16. The flow cytometer of claim 1, further comprising an additional light source configured to illuminate the particle as the particle moves along the flow path, wherein the light resulting from the illumination of the particle by the array comprises fluorescence emitted by the particle, and wherein light resulting from illumination of the particle by the additional light source comprises light scattered by the particle.

17. A measurement method, comprising:
illuminating a particle or microsphere at different positions along a flow path of the particle or microsphere with an array of two or more light emitting diodes spaced along said flow path proximate said different positions;
detecting light resulting from said illuminating to produce individual output signals corresponding to said illuminating at the different positions;
combining the individual output signals to produce a single output signal having a signal-to-noise ratio that is greater than a signal-to-noise ratio of the individual output signals; and
processing the single output signal to determine a magnitude of the detected light.

18. The method of claim 17, wherein said illuminating comprises illuminating the particle or microsphere with one or more arrays of light emitting diodes arranged along the flow path of the particle or microsphere, and wherein the one or more arrays are configured to continuously illuminate the particle or microsphere during an illumination time period as the particle or microsphere moves along the flow path.

19. The method of claim 17, wherein said illuminating comprises illuminating the particle or microsphere at the different positions with approximately the same wavelength or wavelengths of light.

20. The method of claim 17, wherein said illuminating comprises illuminating the particle or microsphere at the different positions at approximately the same angle of illumination.

21. The method of claim 17, wherein said illuminating comprises illuminating the particle or microsphere at the different positions with a series of discrete light pulses.

22. The method of claim 17, wherein said illuminating comprises illuminating the particle or microsphere at the different positions with two or more arrays of light emitting diodes configured to produce light having different wavelengths.

23. The method of claim 17, wherein the single output signal has a pulse length that is greater than a pulse length of each of the individual output signals.

24. The method of claim 17, further comprising collecting the light resulting from said illuminating and directing the collected light directly onto a photosensitive surface of one or more detectors, wherein the one or more detectors perform said detecting.

25. The method of claim 17, wherein said detecting comprises detecting the light resulting from said illuminating with one or more detectors.

26. The method of claim 17, wherein the light resulting from said illuminating comprises fluorescence emitted by the particle or microsphere.

27. The method of claim 17, wherein the light resulting from said illuminating comprises light scattered by the particle or microsphere.

28. The method of claim 17, wherein the light resulting from said illuminating comprises fluorescence emitted by the particle or microsphere and light scattered by the particle or microsphere.

29. The method of claim 17, wherein said processing comprises integrating the single output signal over time to determine the magnitude of the detected light resulting from the illumination of the particle or microsphere.

30. The flow cytometer of claim 1, wherein the processor is further configured to integrate the single output signal over time to determine a magnitude of the detected light resulting from the illumination of the particle.

31. The flow cytometer of claim 1, wherein individual light emitting diodes of the array are configured to illuminate the particle at different positions along the flow path.

32. The flow cytometer of claim 1, wherein individual light emitting diodes of the array are positioned in a two-dimensional array such that a first portion of the individual light emitting diodes are configured to illuminate the particle at different positions along the flow path at approximately the same angle of illumination and such that a second portion of the individual light emitting diodes are configured to illuminate the particle at one of the different positions along the flow path at different angles of illumination.

33. The flow cytometer of claim 4, wherein the individual light emitting diodes are further configured to illuminate the particle at the multiple positions with different wavelengths of light.

34. The flow cytometer of claim 7, wherein the one or more additional arrays are configured to illuminate the particle as the particle moves along the flow path with a wavelength of light that is different than a wavelength of light of the array.

35. The flow cytometer of claim 7, wherein the one or more additional arrays are configured to illuminate the particle as the particle moves along the flow path at an angle of illumination that is different than an angle of illumination of the array.

36. The flow cytometer of claim 1, further comprising one or more additional arrays of light emitting diodes, wherein the array and the one or more additional arrays are arranged along the same portion of the flow path.

37. The flow cytometer of claim 36, wherein the one or more additional arrays are configured to illuminate the particle as the particle moves along the flow path with a wavelength of light that is different than a wavelength of light of the array.

38. The flow cytometer of claim 36, wherein the one or more additional arrays are configured to illuminate the particle as the particle moves along the flow path at an angle of illumination that is different than an angle of illumination of the array.

39. The flow cytometer of claim 1, further comprising one or more lenses configured to collect the light resulting from the illumination and to direct the collected light onto a photosensitive surface of the one or more detectors indirectly using one or more fiber optic cables.

40. The method of claim 17, wherein said illuminating comprises illuminating the particle or microsphere at one of the different positions at multiple angles of illumination with multiple individual light emitting diodes.

41. The method of claim 40, wherein the multiple individual light emitting diodes generate light of substantially the same wavelength.

42. The method of claim 40, wherein the multiple individual light emitting diodes generate light of different wavelengths.

43. The method of claim 17, wherein the different positions are arranged along a first portion of the flow path, wherein said illuminating comprises illuminating the particle or microsphere at the different positions with a first wavelength of light, the method further comprising illuminating the particle or microsphere at additional positions along a second portion of the flow path of the particle or microsphere with a second wavelength of light different than the first wavelength of light.

44. The method of claim 17, wherein the different positions are arranged along a first portion of the flow path, wherein said illuminating comprises illuminating the particle or microsphere at the different positions at a first angle of illumination, the method farther comprising illuminating the particle or microsphere at additional positions along a second portion of the flow path of the particle or micro sphere with a second angle of illumination different than the first angle of illumination.

45. The method of claim 17, wherein said illuminating comprises illuminating the particle or microsphere at the different positions with two or more arrays of light emitting diodes arranged at different angles of illumination.

46. The method of claim 17, wherein said illuminating comprises illuminating the particle or microsphere at the different positions with two or more arrays of light emitting diodes arranged at different angles of illumination, wherein the two or more arrays are configured to illuminate the particle or microsphere with a different wavelength of light at each of the different angles of illumination.

47. The method of claim 17, further comprising collecting the light resulting from said illuminating and directing the collected light indirectly onto a photosensitive surface of one or more detectors using one or more fiber optic cables, wherein the one or more detectors perform said detecting.

* * * * *

UNITED STATES PATENT AND TRADEMARK OFFICE
CERTIFICATE OF CORRECTION

PATENT NO. : 7,692,773 B2  Page 1 of 1
APPLICATION NO. : 10/896181
DATED : April 6, 2010
INVENTOR(S) : Wayne D. Roth It is certified that error appears in the above-identified patent and that said Letters Patent is hereby corrected as shown below:

Col. 20, line 29, delete "farther" and substitute --further--.

Col. 20, line 31, delete "micro sphere" and substitute --microsphere--.

Signed and Sealed this

Eighteenth Day of May, 2010

David J. Kappos
*Director of the United States Patent and Trademark Office*